Jan. 10, 1961 G. MERRILL Plant Pat. 2,010

NECTARINE TREE

Filed Feb. 29, 1960

WITNESS

Addison E. Avery

INVENTOR

GRANT MERRILL

HUEBNER & WORREL, ATTORNEYS

BY Richard M. Worrel

United States Patent Office

Plant Pat. 2,010
Patented Jan. 10, 1961

2,010

NECTARINE TREE

Grant Merrill, Red Bluff, Calif.

Filed Feb. 29, 1960, Ser. No. 11,941

1 Claim. (Cl. 47—62)

The present invention relates to a nectarine tree and more particularly to a new and distinct variety thereof broadly characterized by being a large heavy producing tree which bears large, intensely red, firm, thick skinned, yellow fleshed nectarines. The nectarines are semi-free stone when ripened off of the tree, and ripen at the same time to five days earlier than Merrill Princess (Plant Patent No. 1,410) varying somewhat in different years. The new variety nectarine tree is an improvement over the Merrill Princess in being larger, more vigorous, and more productive and in bearing fruit that is larger, more nearly spherical and thicker skinned.

Because of rich soil and favorable climatic environment prevailing in most of the commercial nectarine farming areas of California, the nectarine trees tend to produce rank growth and dense shade resulting in serious impairment of the coloring of the fruit. Inasmuch as most fruits rely on eye appeal for their sales, color impairment is highly undesirable. A primary object to the plant breeding procedures which have resulted in the development of this new nectarine variety has been to achieve a highly colored red nectarine which maintains its color even under conditions of rank growth and dense shade.

A collateral object has been to produce a new nectarine variety characterized by moderate but consistent fruit set which minimizes pruning and thinning requirements without being subject to irregular production.

Further objects and advantages will become apparent in the subsequent description in the specification.

Figure 1:
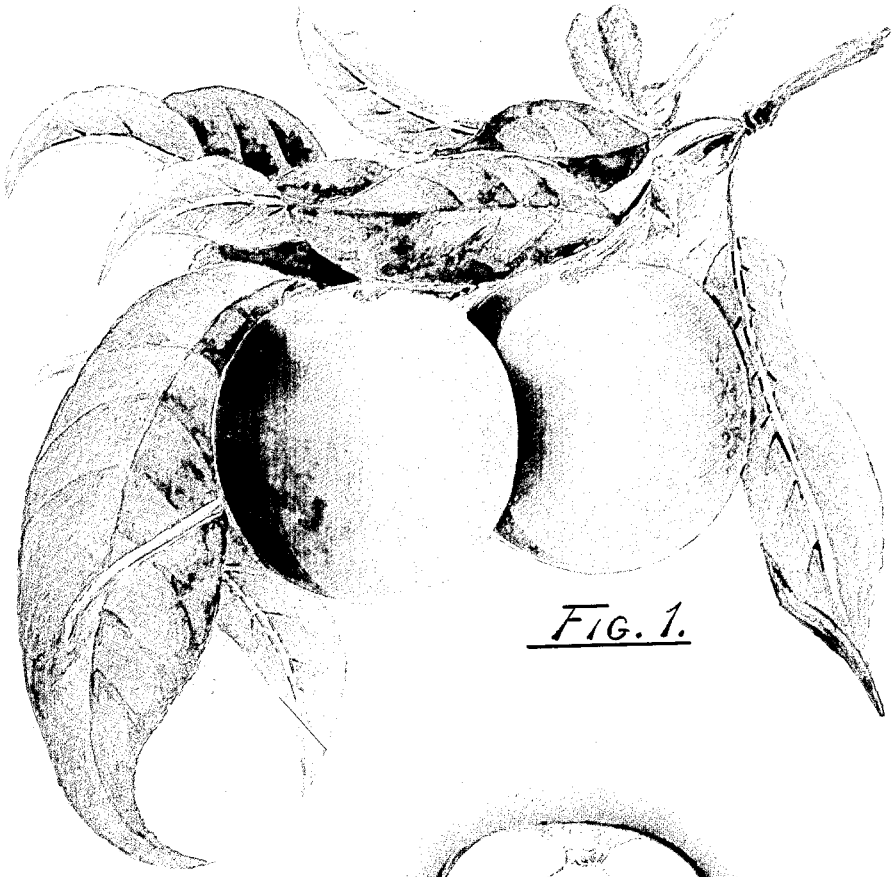
Fig.1 is a water color painting of characteristic fruit bearing twig of the subject nectarine tree having leaves and mature nectarines thereon.
Figure 2:
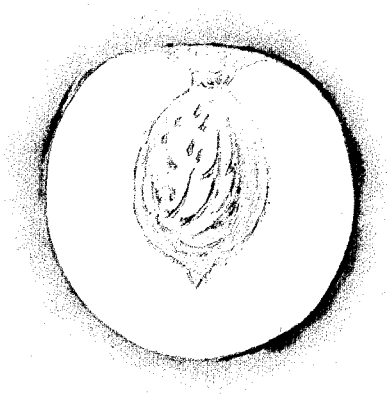
Fig. 2 is a water color painting showing a characteristic fruit of the subject nectarine tree divided on its suture plane to reveal flesh coloration and showing a pit in place therein.

The most distinctive characteristics in the instant variety of nectarine tree are its large size and heavy production for its season, and its production of large, firm, yellow fleshed, highly colored, thick skinned nectarines that are semi-freestone when ripened off the tree.

The instant variety most nearly resembles Merrill Princess nectarine (Plant Patent No. 1,410) but is an improvement thereon in that the tree is more vigorous and heavy producing and the fruit is larger and more round and the skin is thicker.

This new variety of nectarine was produced by me on my farm near Red Bluff, Tehama County, California by crossing J. H. Hale (unpatented) and Flaming Gold nectarine (unpatented) followed by two generations of open pollinated seedlings therefrom.

The present variety was asexually propagated by grafting onto a tree of Merrill June (Plant Patent No. 869) growing on my farm at Lamont, Kern County, California. When this graft came into bearing, fruit and other characteristics of this nectarine tree proved to be identical with the original nectarine tree.

Referring more specifically to the pomological characteristics of this new and distinct variety of nectarine tree, the following have been observed under the ecological conditions prevailing at my farms near Red Bluff, Tehama County California, and Lamont, Kern County, California, and is an outline description thereof. All major color plate identifications are by reference to Maerz and Paul Dictionary of Color.

*Tree*

Shape: Large, vigorous, with medium spread, productive and regular bearer.

Trunk: Medium stocky, medium shaggy, brownish grey.

Branches: Older branches, greyish and shaggy; younger branches, brown to medium brown and more smooth, with numerous, medium size lenticels.

Leaves (selected from midportion of vigorous unbranched terminal shoots 18" to 24" long):

*Length.*—5½" to 7", average 6".

*Width.*—1½" to 1¾", average 1⅝".

*Form.*—Medium size, lanceolate, tip acuminate, medium thick.

*Color.*—Upper surface of leaf medium green (23–L–7). Under surface of leaf lighter green (23–J–6). Heavy under midrib greenish yellow (17–J–1).

*Class* (Meader and Blake: Proceedings: Am. Soc. Hor. Sc., vol. 37, page 206).—2 to 3. Width—length ratio .25. Apex angle (1" from tip)—40° to 43°, average 41°. Base angle (½" from petiole)—60° to 63°, average 61°.

*Margin.*—Crenate.

*Petiole.*—Medium length, medium slender.

*Stipules.*—At base of leaf, falling off early.

*Glands.*—0 to 4, average 2, mostly opposite and alternate, medium small size, reniform, reddish brown, position, on petiole and base of leaf.

Flower buds: Medium size, medium length, plump, free, pubescent.

Flowers: Bloom about midseason, about in the season with Fay Elberta (unpatented), large, showy, pink.

*Anthers.*—Dehiscence, orange.

*Pollen.*—Moderately abundant.

*Fruit*

Maturity when described, firm to hard ripe.

Size: Large.

*Axial diameter.*—2" to 2½", average 2¼".

*Transverse in suture plane.*—2" to 2⅝", average 2 3/16".

*At right angles to suture plane (cheek to cheek).*—2" to 2⅝", average 2 5/16".

Form: Very symmetrical, nearly globose.

*Suture.*—Shallow, extends from base to beyond, but discontinuous at apex. Slight depression beyond pistil point.

*Ventral surface.*—Rounded, slightly ridged on either side.

*Cavity.*—Moderately rounded, abrupt, generally circular, only slightly elongated in suture plane, with suture showing slightly on the dorsal side, and conspicuous on the ventral side. Depth about ½", breadth about ½". Markings—mostly green with some dark red to some all red.

*Base.*—Retuse.

*Apex.*—Emarginate to truncate.

*Pistil point.*—Inconspicuous to none.

*Stem.*—Short, less than ¼", diameter ⅛", adhere to stone in many cases.

*Skin.*—Thick, rough, tenacious to flesh. Color—orange yellow (9–L–5) with blush from a light red orange (1–E–12) grading through to a darker orange (11–K–11) to a red (5–L–5) and darkening to a dark red (7–L–5).

Flesh:

*Color.*—From greenish yellow near the stem end (10–L–1) to an orange yellow over most of the area of the flesh (9–L–6) to a deeper orange yellow (9–K–7).

*Amygadalin.*—Moderate.

*Juice.*—Abundant, rich.

*Texture.*—Firm, fine, meaty.

*Fibers.*—Few, fine, tender.

*Ripens.*—Fairly evenly, but slightly earlier at the apex.

*Flavor.*—Sub-acid, mild, vinous.

*Aroma.*—Moderate.

*Eating quality.*—Good.

Stone: Semi-free when ripened off the tree, cling when firm ripe or when ripened on the tree. Fibers almost absent.

*Size.*—Medium. Length 1″ to 1½″, average 1¼″. Breadth ¾″ to 1¼″, average 1″. Thickness ¾″ to 1″, average ⅞″.

*Form.*—Mostly obovate, tip acuminate.

*Base.*—Mostly straight.

*Hilum.*—Oval.

*Apex.*—Acuminate.

*Sides.*—Mostly equal, few unequal and flattened on either side.

*Surface.*—Irregularly furrowed at the center of each side and along the dorsal and ventral edges and near apex. Pits elongated, ventral edge without wing, dorsal edge with deep groove from base to near the apex. Ridges on either side interrupted.

*Color.*—Pinkish tan (9–A–6).

*Tendency to split.*—Little.

Use: Market, local, dessert, culinary, long distance shipping.

Shipping and keeping quality: Good.

It is to be understood that normal variations in the described characteristics of the new variety nectarine tree result from environmental changes, such as in climate and soil conditions, and from changes in cultural practices, such as in pruning, thinning, fertilizing, spraying, irrigating, and the like. The description is that of the variety produced under the ecological conditions prevailing at my farms at Lamont, Kern County and Red Bluff, Tehama County, California and the characteristics are found to hold true in asexual reproduction of the variety.

Having described and illustrated my new variety of nectarine tree, what I claim as new and desire to secure by Letters Patent is:

A new and distinct variety of nectarine tree, substantially as illustrated and described, characterized by its large size and heavy production; its bearing of firm, yellow fleshed, intensely red, thick skinned, large, nectarines which are semi-freestone when ripened off the tree, and which ripen at the same time to five days earlier than fruit of the Merrill Princess nectarine tree (Plant Patent No. 1,410); and which is further distinguished from the Merrill Princess nectarine tree and an improvement thereover in its greater vigor and productivity and by the production of larger and more nearly spherical fruit having thicker skin.

No references cited.